United States Patent [19]

Talish et al

[11] Patent Number: 5,003,965
[45] Date of Patent: Apr. 2, 1991

[54] MEDICAL DEVICE FOR ULTRASONIC TREATMENT OF LIVING TISSUE AND/OR CELLS

[75] Inventors: Roger J. Talish, Fairfield; Arthur L. Lifshey, East Brunswick, both of N.J.

[73] Assignee: Meditron Corporation, Spring Valley, N.Y.

[21] Appl. No.: 247,105

[22] Filed: Sep. 14, 1988

[51] Int. Cl.$^5$ .............................. A61B 17/56
[52] U.S. Cl. ..................... 128/24 AA; 310/316; 310/345; 310/348
[58] Field of Search ......... 128/24 AA, 660.03, 419 F; 310/316, 345, 348

[56] References Cited

U.S. PATENT DOCUMENTS

| | | | |
|---|---|---|---|
| 2,460,153 | 1/1949 | Smoluchowski | 310/348 |
| 2,763,153 | 9/1956 | Simjian | 128/662.03 |
| 3,142,492 | 6/1973 | Proctor | 310/316 |
| 3,805,509 | 4/1974 | Assmus et al. | 310/345 |
| 4,216,462 | 8/1980 | McGrath et al. | 128/710 |
| 4,296,753 | 10/1981 | Goudin | 128/662.03 |
| 4,315,503 | 2/1982 | Ryaby et al. | 128/419 F |
| 4,368,410 | 1/1983 | Hance et al. | 128/24 A |
| 4,530,360 | 7/1985 | Duarte | 128/419 F |
| 4,536,673 | 8/1985 | Forster | 310/345 |
| 4,574,809 | 3/1986 | Talish et al. | 127/419 F |
| 4,708,127 | 11/1987 | Abdelghani | 128/24 A |

FOREIGN PATENT DOCUMENTS 8800845  2/1988  PCT Int'l Appl. .......... 128/419 F

*Primary Examiner*—Lee S. Cohen
*Assistant Examiner*—John D. Zele
*Attorney, Agent, or Firm*—Hopgood, Calimafde, Kalil, Blaustein & Judlowe

[57] ABSTRACT

The invention contemplates an ultrasonic body treatment system wherein a body applicator is self-contained unit with its own radio-frequency oscillator/driver, factory-pretuned to its own transducer. A remote-control unit supplies control signals via optical coupling to the oscillator-driver of the body-applicator unit. Another optical coupling from the body-applicator unit to the remote-control unit enables fidelity of applicator performance to be monitored at the remote-control unit. A safety interlock at the body-applicator unit precludes transducer operation in the absence of adequate coupling to a patient's body. The remote-control unit can thus provide all supervisory and control functions for the body-applicator unit without any electrical interconnection between these units.

28 Claims, 2 Drawing Sheets

MEDICAL DEVICE FOR ULTRASONIC TREATMENT OF LIVING TISSUE AND/OR CELLS

BACKGROUND OF THE INVENTION

The invention relates to use of ultrasonic radiation at relatively low levels into living tissue, as for the non-invasive healing treatment of bone fractures, pseudarthroses and the like.

Duarte Patent No. 4,530,360 describes a technique of treating bone defects of the character indicated using a pulsed radio-frequency ultrasonic signal applied via a transducer to the skin of a patient and directed to the site of the defect. The radio-frequency signal is in the range of 1.3 to 2 MHz, and it consists of pulses at a repetition rate of 100 to 1,000 Hz, with each pulse having a duration in the range 10 to 2,000 microseconds. The Duarte apparatus comprises a radio-frequency oscillator connected to a driver, and a pulse generator is arranged to control driver output in accordance with a preselected duration and repetition rate of bursts of radio-frequency oscillations in the driver output. A flexible radio-frequency cable connects driver output to a body applicator, in the form of a hand-held plastic tube, one end of which is closed to mount a piezoelectric transducer, in the form of a thin flat disc, excited for thickness resonance.

Necessarily, therefore, in the Duarte apparatus, the source of electrical energy is remote, as on a table top, and the flexible connection to the body applicator must, in use, always be electrically "live"; (i.e., electrically common to the remote source and to the body applicator) and, therefore potentially hazardous. Also, for the power levels involved, and considering the fact that two or more transducers seldom can be found to resonate at precisely the same frequency, the radio-frequency must be pretuned to serve one and only one transducer. In other words, the apparatus of the Duarte patent necessarily dedicates the remote signal-generating part of the system to the particular applicator. Any attempt to replace a damaged applicator must involve a retuning of the signal-generator to the newly substituted applicator.

BRIEF STATEMENT OF THE INVENTION

It is an object of the invention to provide an improved apparatus of the character indicated.

It is a specific object to avoid flexible-cable transmission of radio-frequency or other electrical signals in such apparatus.

Another specific object is to avoid the need for retuning the apparatus when replacing a body applicator.

A further specific object is to provide an improved body applicator which lends itself to treatment of damaged bone tissue, as within an orthopedic cast, or as in a strapped application to a body part.

Still another specific object is to meet the above objects with apparatus involving no transmission of electrical energy between the remote-control unit and the body applicator.

A still further specific object is to provide improved remote-control apparatus in conjunction with improved body-applicator apparatus whereby plural body applicators can be served by a single unit of the remote-control apparatus.

A general object is to meet the above objects with apparatus of relatively simple and inexpensive construction, and presenting minimum radio-frequency or other electrical hazard in use.

The invention meets the above objects by providing the body applicator as a self-contained unit with its own radio-frequency oscillator/driver, factory-pretuned to its own transducer, and by limiting the remote-control unit to the supply of control signals via optical coupling to the oscillator/driver of the body-applicator unit. Another optical coupling from the body-applicator unit to the remote-control unit enables fidelity of applicator performance to be monitored at the remote-control unit. A safety interlock at the body-applicator unit precludes transducer operation in the absence of adequate coupling to a patient's body. The remote-control unit can thus provide all supervisory and control functions for the body-applicator unit without any electrical interconnection between these units.

DETAILED DESCRIPTION

The invention will be described in detail in conjunction with the accompanying drawings, in which.

Figure 1:
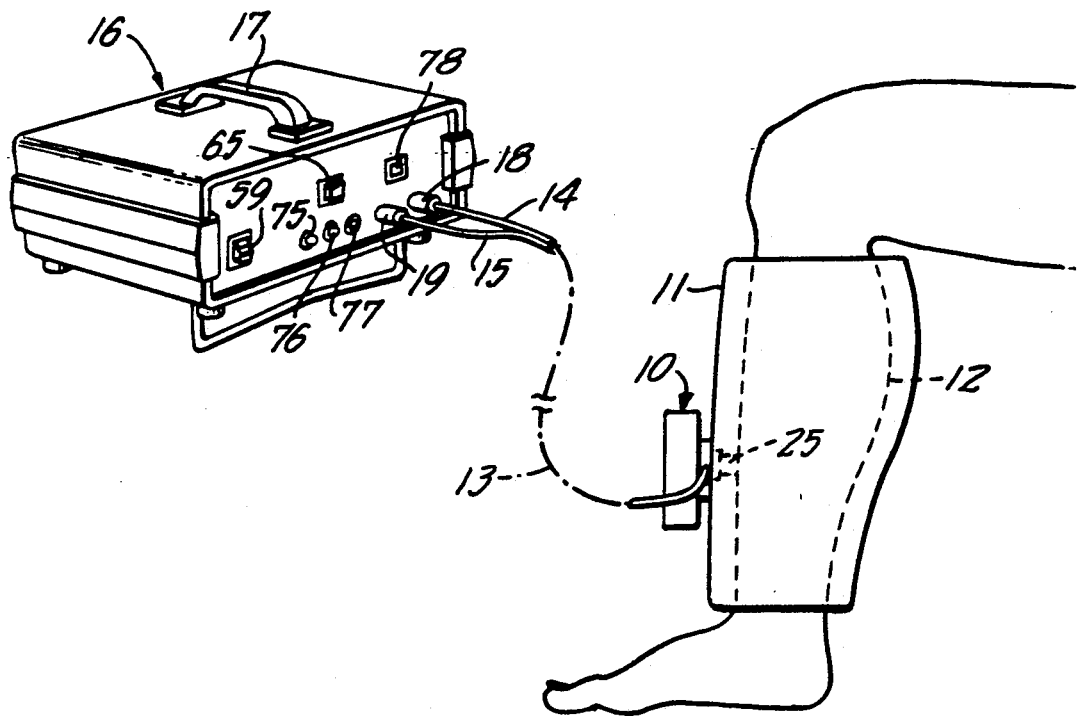
FIG. 1 is an overall view of flexibly connected remote-control and body-applicator units of the invention, in the context of providing ultrasonic treatment to damaged bone tissue within an orthopedic cast.

In FIG. 1, a body-applicator unit (or treatment head) 10 of the invention is shown mounted to an orthopedic cast 11 for treatment of a bone injury or defect in a human leg 12. A flexible cable 13 comprising separately sheathed fiber-optic lines 14, 15 connects the body-applicator unit 10 to a remote-control unit 16, which may be relatively compact and portable, as suggested by a carrying handle 17; and detachable connectors 18, 19 of optical-transmission lines 14, 15 to the front panel of remote-control unit 16.

The electrical contents, within plug into the housing 20 of the body-applicator unit 10, will be later described in detail, but it suffices for present purposes to state that housing 20 contains storage batteries and a circuit board 21 of oscillator/driver components, with flexible shielded-lead connections 22, 23 to a thin, flat transducer element 24. Element 24 may be a commercially available piezoelectric ceramic disc, as of the lead-zirconium-titanate material known as PZT-4. Element 24 will be understood to include a separate foil electrode bonded to each of its front and back surfaces, to enable thickness fluctuation in response to driven excitation via connections 22, 23. Transducer 24 is bonded to the inner surface of the closed end wall of a cupped shell 25 having a base flange 26. An inner wall 27 is secured to shell 25 and is spaced from and behind transducer 24, to provide a seat for softly yielding compliant suspension of shell 25 and transducer 24 via a cylindrical body 28 of foamed plastic.

Figure 3:
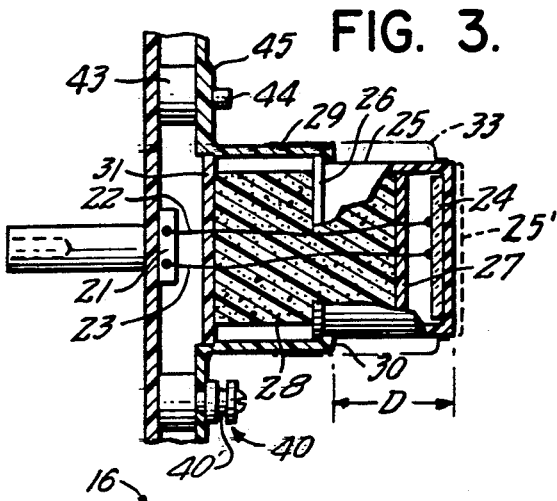
FIG. 3 is a fragmentary section which includes the central axis of the transducer and its support, in the body-applicator unit of FIGS. 1 and 2, the section half above the central axis and the section half below the central axis being taken in separate orthogonally related planes which intersect along the central axis.
Figure 4:
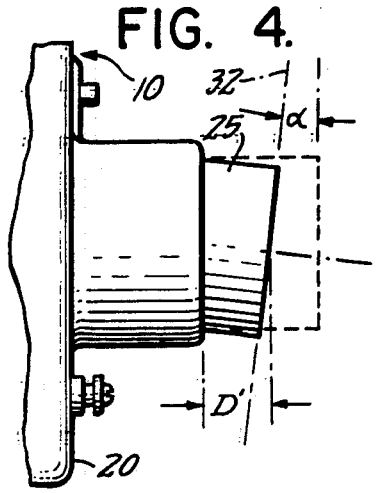
FIG. 4 is a fragmentary side view in elevation, for the aspects of FIG. 3, to show transducer accommodation to a body surface.

To provide suspension support for shell 25 and transducer 24, housing 20 is integrally formed with a tubular projecting cylindrical wall 29 having an inturned flange 30 at its outer end, for engagement with flange 26, thus outwardly limiting shell-25 projection to the extent D beyond the open end of the projecting wall 29, as shown in FIG. 3. At the base end of the wall 29, a panel 31 secured to housing 20 provides a seating base for the other axial end of the compliant body 28 of foamed plastic. The described mounting of transducer 24 will be seen to provide an axially compliant suspension, with gentle yielding for axially inward deflection, and with a generous degree of axial misalignment capability, away from the axis of wall 29, all as suggested in FIG. 4 for the case of a misalignment angle o and reduced projecting offset D', when in self-adapting application to a local patient-body surface 32.

A phantom outline at 33 will be understood to indicate the preferred use of a flexible plastic sleeve, as of vinyl or silicone, circumferentially bonded to the axially outer rim of shell 25 and having sliding overlap with the cylindrical wall 29. Sleeve 33 in no way interferes with the misalignability described in connection with FIG. 4, but it does protect against entry of foreign matter via the running fit of shell 25 to the opening of housing flange 30.

At spaced locations about the base end of the projecting cylindrical wall 29, housing 20 is provided with means for co-action with corresponding features of an expendable mounting fixture 35, which may be of injection-molded plastic but which can also be suitably formed by thermal slumping from plastic sheet material of suitable gauge. Fixture 35 is expendable because it is designed for embedded incorporation in an orthopedic cast, as at a locally cut access opening in stockinette, prior to development of the retaining plaster of the cast.

Figure 2:
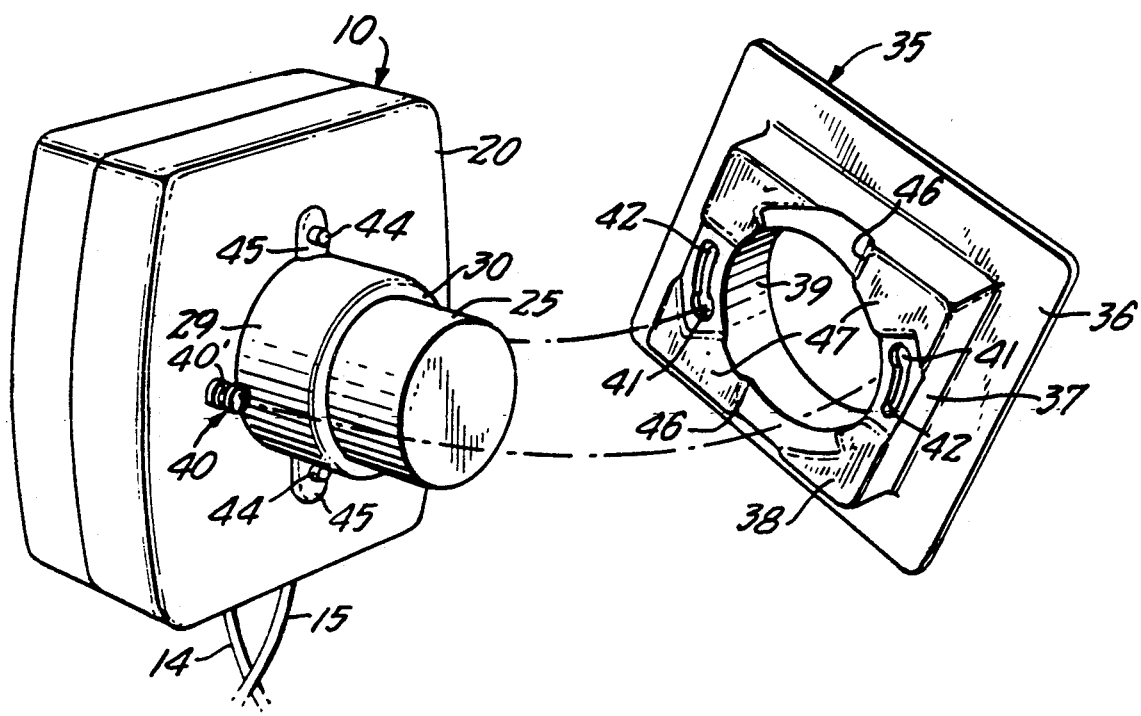
FIG. 2 is an enlarged view in one perspective of the body-applicator unit of FIG. 1 and in an image-reversed perspective of an embedment fixture, said fixture being for embedment in the cast of FIG. 1 and for detachable mounting reception of the body-applicator unit.

As shown in FIG. 2, fixture 35 is of generally rectangular outline, providing an outward flange 36 which extends peripherally around a truncated-pyramid wall 37 which positions its truncation face 38 for confronting acceptance of and removably retained engagement with the transducer-supporting side of the body-applicator unit 10. The offset extent of face 38 from flange 36 is in the order of one centimeter, to enable adequate building of casting plaster above flange 36.

The center of face 38 is characterized by an opening defined by an integrally formed cylindrical flange 39 for insertional telescopically piloting acceptance of the cylindrical wall 29 of unit 10. The preferred engagement to unit 10 is of bayonet-locking variety, being shown on housing 20 to comprise two outwardly projecting studs 40 at diametrically opposite but radially equal offset locations on housing 20, with respect to the central axis of the projecting cylindrical wall 29. Studs 40 are enterable into diametrically opposite enlargements 41, at corresponding ends of arcuate and narrowed slots 42; and studs 40 are circumferentially grooved at 40' to accomondate local fixture thickness at face 38. Thus, once studs 40 are inserted at 41, unit 10 may be bodily rotated with respect to fixture 35 to complete the bayonet-locking engagement of studs 40 to slots 42.

The upper half-section of FIG. 3 additionally shows that, at diametrically opposite locations which are at 90° -offset from studs 40, the transducer side of housing 20 also mounts two normally open switches 43 having actuator buttons 44 which project outwardly but which, upon inward depression (as when the bayonet-locking engagement is effected) will close their respective contacts. These contacts will be understood to provide a safety-interlock feature, operative upon circuitry within unit 10, whereby no battery power can be supplied to the oscillator/driver in the absence of concurrent closure of both switches 43.

To assure frictional retention of the bayonet-locked engagement, FIGS. 2 and 3 show switch actuator buttons 44 to project beyond local land formations 45 of housing 20, and these land formations ride up cam or ramp slopes 46 to lands 47 in the face 38 of fixture 35, in the course of the relative rotation which moves studs 40 from entry openings 41 and into their other or "home"-'engagement positions in arcuate slots 42. After such ramping, slot-42 engagements in the grooves of studs 40 retain an axial bias of the frictional engagement between lands 45, 47.

Figure 5:
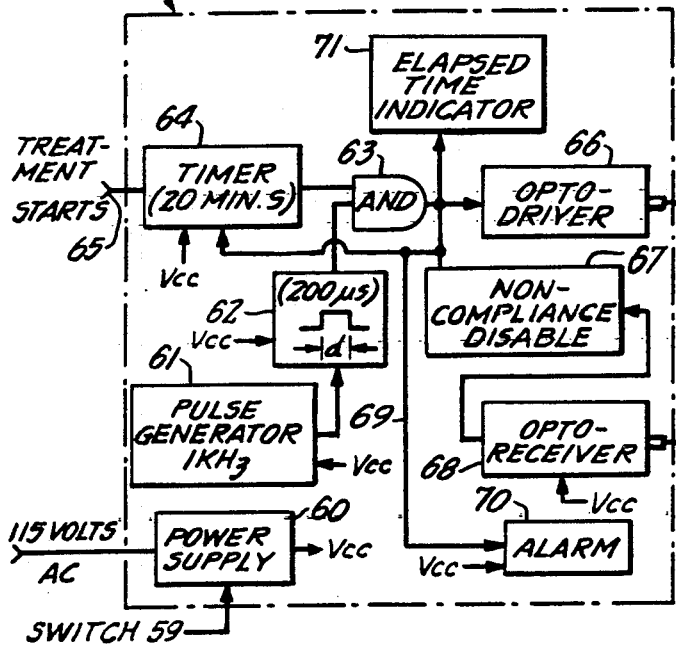
FIG. 5 is a block diagram of electrical and optical components of the apparatus of FIG. 1.
Figure 5:
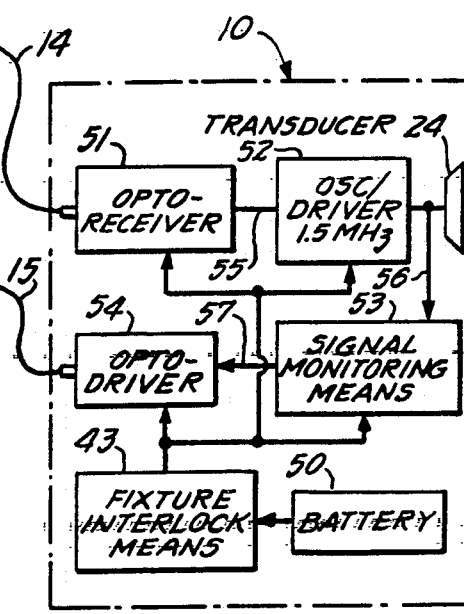

In the diagram of FIG. 5, the body-applicator unit 10 is seen to contain battery means 50 which, subject to closure of the safety-interlock switching means 43, supplies power for local operation of (a) an opto-receiver 51, (b) an oscillator/driver 52 that is specifically tuned for optimum coupling to transducer 24, (c) signal-monitoring means 53, and (d) an optodriver 54. The opto-receiver 51 may be a photodiode which receives control pulses via optical-fiber line 14 from the remote-control unit 16 and which provides (in line 55) corresponding electrical-pulse output for on/off control of the oscillator/driver 52 and, therefore, for on/off control of transducer 24 operation. A connection 56 enables the signal-monitoring means 53 to provide an output signal in line 57 to opto-driver 54, which may be a light-emitting diode, whereby the monitoring signal may be transmitted via fiber-optic line 15 back to the remote-control unit 16. The parenthetic legend "1.5 MHz" at 52 in FIG. 5 will be understood only to be typical of the tuned frequency at which it is to operate, due to physical thickness-resonance properties of the particular transducer 24 which it is connected to drive, such tuned frequency being generally within the range 1.3 to 2.0 MHz.

At and within the remote-control unit 16, local power-supply means 60 operate from externally available household-voltage supply, and its single showing of output "VCC" will be understood to schematically designate local power supply as necessary for all electronic components within unit 16, subject to switching via an on/off toggle 59 at the front panel of unit 16. Thus powered, a pulse generator 61, in conjunction with a pulse-width controlling device 62, which may be a one-shot multivibrator, develops control pulses of predetermined width and repetition rate, for ultimate on/off operation of the oscillator/driver 52 of the body-applicator unit 10. As shown, such operation can only proceed as long as an AND device 63 certifies that it is receiving, from a treatment timer 64, a signal indicating that the treatment time, initiated by a "start" button 65, has not yet been timed out. Pulsed output of AND device 63 is delivered directly to an opto-driver 66, which may be a light-emitting diode coupled for transmission of corresponding light pulses in fiber-optic line 14 to unit 10.

Within the body-applicator unit 10, a further function of the signal-monitoring means 53 is to test for compliance (with the intended signal transmission to the patient). Specifically, (a) if the signal changes, or (b) if the battery output is less than a predetermined operating level, then a "no-compliance" signal is sent to the control unit 16, via fiber-optic connection 15 to "Non-Compliance/Disable" means 67 in unit 16; the function of means 67 is to allow only the correct intended signal to be sent (by opto-driver 66 and fiber-optic connection 14) to the applicator unit 10. As to (a) above, a signal change which exceeds a predetermined value will be understood to reflect failure of the active face of transducer 24 to achieve a predetermined level of efficiency in the coupling of ultrasonic energy to the intended body tissue. Thus, if coupling means, such as a gel 25'0 interposed between the transducer wall of shell 25 and adjacent body tissue, provides insufficient coupling, whether through use of an insufficient quantity of gel, or if a plaster fragment interferes with full resiliently loaded application of the profile-adapting action (as in FIG. 4), the signal-monitoring means will detect the coupling insufficency and will communicate the same to the non-compliance/disable means 67 of the control unit 16, for an automatic shut-down of the operation, via a "shut-down" signal in line 69. An alarm circuit 70 is shown connected for operation in response to this detected circumstance. Finally, an elapsed-time indicator 71 (which need not externally display its current value indication) is shown connected separately to the output line of control-pulse transmission and to the non-compliance/disable means 67, whereby total treatment time at 71 will reflect tally of increments of treatment time only as long as the signal pulses monitored at 53 have been found to compare favorably with intended signal transmission to the patient. Time-out of a treatment period at 4 will foreclose AND-circuit passage of control pulses to opto-driver 66, thus foreclosing time advance at elapse-time indicator 71. Also, failure to close both switches 43 is operative to disable battery (50) supply to the various components of unit 10, thereby foreclosing monitor 53 from detecting compliance and also therefore foreclosing time advance at indicator 71.

The parenthetic indication of a 1-KHz pulse-repetition rate at 61 and of a 200-microsecond control-pulse duration at 62 will be understood to be typical and illustrative but not necessarily critical, in that, as taught by *Duarte*, pulse-repetition rate may suitably be in the range between 100 and 1,000 Hz, and control-pulse duration may suitably be in the range between 10 and 2,000 microseconds. Also the 20-minute treatment time, indicated at 64, will be understood to be typical, for one treatment per day, in that other treatment times and number of treatments per day may also be therapeutically beneficial. Generally, and desirably, the average intensity of ultrasonic energy delivered to the body is in the range of 1 to 50 milliwatts/cm$^2$.

Figure 6:
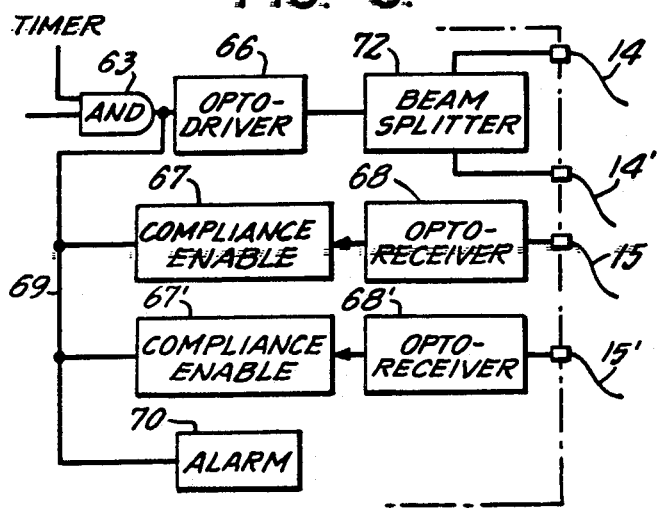
FIG. 6 is a fragmentary block diagram to illustrate a modification.

Although fiber-optic flexible transmission lines have been shown as the preferred technique and coupling between control unit 16 and the body-applicator unit 10, this is only illustrative. For example, if the patient is one of several who are bed-ridden and unable to move, then there is no reason why the controlling light pulses could not be transmitted by directed beam to the receiving device 51 of each of a plurality of body-applicator units. By the same token, the control unit 16 can provide control-pulse sourcing and compliance-monitoring functions for each of a plurality of body-applicator units that are optically coupled to the same control unit 16. The fragmentary diagram of FIG. 6 illustrates such a situation wherein the components 63, 66, 67, 68 and 70 of FIG. 5 can be recognized for their corresponding functions in FIG. 6; essentially the only difference is suggested by beam-splitter means 72 which divides the pulsed-light output of driver 66 into separate lines of connection to fiber-optic control lines 14, 14' to the respective plural units 10. Similarly, fiber-optic lines 15, 15' from the separate units 10 are served by separate opto-receivers 68, 68' and by separate compliance monitors 67, 67', each of which derives its conformance reference from the same control-pulse line 69.

Description of the front panel of control unit 16 is completed by identifying different-color indicator lamps 75, 76, 77 which are indicative of current system status. For example, a "standby" lamp 75 may be amber and indicative of current operation within the treatment-time period of timer 64; a "complete" lamp 76 may be blue and indicative of completion of the treatment period time at 64; and a "trouble" lamp 77 may be red and indicative of a non-compliance detection at 67. Finally, an "active" indicator lamp at 78 may be green and indicative of readiness to commence a timed treatment.

Although the use of light pulses for communication between units 16 and 10 has been described without reference to specific wavelengths, it is to be understood that for particular purposes infrared-transmission may be more desirable than visible-light transmission, or vice versa; thus, LED devices may be used for transmission, in visible-light applications, or in infrared-transmitting applications; alternatively, laser devices may be used with digitally coded information, using currently available technology.

What is claimed is:

1. For use in the treatment of living tissue and/or cells with ultrasonic radiation, a self-contained treatment-head unit comprising a housing having an external-access port, an ultrasonic generator and a power source connected to said generator and contained within said housing, an ultrasonic transducer connected to said generator and having an active body-application face exposed externally of said housing, said generator being specifically tuned for efficient coupling to said transducer, and control means for said generator including photo-sensitive device means carried within said housing and adapted via said port to produce electrical-control signals governing operation of said generator.

2. The unit of claim 1, in which said housing has a second external-access port and in which signal-monitoring means is contained within said housing and is connected to said generator, said signal-monitoring means including means for detecting a generator-output signal change which exceeds a predetermined value and for producing a monitor-output signal upon detection of such change, and means including a light source, said means being adapted via said second port for externally and optically communicating said monitor-output signal.

3. The unit of claim 2, in which said housing includes, at said second part, adapter means for detachably coupling an optical fiber to light from said light source.

4. The unit of claim 1, wherein sound coupling means is interposed between the transducer and body tissue for ultrasonic communication with body tissue.

5. The unit of claim 4, wherein said sound-coupling means is a gel.

6. The unit of claim 4, in which signal monitoring means is provided in said housing for detection of a failure to achieve a predetermined level of efficiency in the coupled transmission of ultrasound output to the body tissue, said signal monitoring means producing an output signal upon such a detected failure.

7. For use in the treatment of living tissue and/or cell with ultrasonic radiation, a self-contained treatment-head unit comprising a housing having an external-access port, an ultrasonic generator and a power source connected to said generator and contained within said housing, an ultrasonic transducer electrically connected to said generator and having an active body-application face exposed externally of said housing, said generator being specifically tuned for efficient coupling to said transducer, and control means for said generator including photo-sensitive device means carried within said housing and adapted via said port to produce electrical-control signals governing operation of said generator, all electrical connections between said power source, said generator, said transducer and said photo-sensitive device being self-contained within said housing.

8. The unit of claim 1 or claim 2, wherein said photo-sensitive device is infrared-sensitive.

9. The unit of claim 1 or claim 2, wherein said photo-sensitive device is sensitve to visible light.

10. The unit of claim 7 or claim 1, wherein said housing includes, at said port, adapter means for detachably coupling an optical fiber to said photo-sensitive device.

11. The unit of claim 7 or claim 1, in which said generator includes an oscillator that is tunable in the range of 1.3 tp 2 megahertz.

12. The unit of claim 7 or claim 1, in which the output intensity level of said transducer when driven by said generator is in the range 1 to 50 milliwatts/cm$^2$.

13. The unit of claim 7 or claim 1, in which said transducer is mechanically isolated from said housing by a softly compliant suspension, said compliant suspension providing a range of local universal angular self-adapting application of the body-application face of said transducer to a body-contour orientation.

14. The unit of claim 1 or claim 1 in combination with a mounting-adaptor unit for incorporation in an orthopedic cast, said adapter unit having a central aperture, and said housing and said adapter unit having coacting locking formations arrayed about said transducer and about said central aperture, whereby upon locking engagement of said treatment-head unit to said adapter unit that has been incorporated into an orthopedic cast, said transducer is held by said treatment-head unit and by said adapter unit in local body-confronting relation to a body locale that is otherwise surrounded by the orthopedic cast.

15. The unit of claim 1 or claim 1, in combination with a mounting-adapter unit for incorporation in an orthopedic cast, said adapter unit having a central aperture, and said housing and said adapter unit having coacting locking formations arrayed about said transducer and about said central aperture, whereby upon locking engagement of said treatment-head unit to said adapter unit that has been incorporated into an orthopedic cast, said transducer is held by said treatment-heat unit and by said adapter unit in local body-confronting relation to body locale that is otherwise surrounded by the orthopedic cast, said transducer being softly compliantly suspended by said housing at projected offset away from said housing, said offset being sufficent to project said transducer through and beyond the central aperture of said adapter unit when in locked assembly thereto.

16. The unit of claim 7 or claim 1, in combiantion with a mounting-adapter unit for incorporation in an orthopedic cast, said adapter unit having a central aperture, and said housing and said adapter unit having coacting locking formations arrayed about said transducer and about said central aperture, whereby upon locking engagement of said treatment-head unit to said adapter unit that has been incorporated into an orthopedic cast, said transducer held by said treatment-head unit and by said adapter unit in local body-confronting relation to a body locale that is otherwise surrounded by the orthopedic cast, at least one normally open unactuated switch being mounted to said housing and including an actuating button which projects outward of said housing for inward switch-closing actuation upon assembly to said adapter unit, and means including a light source having a control connection to said switch and being adapted via a second port in said housing to externally communicate the integrity of assembly of the treatment-head unit to the adapter unit, whereby electrically operation of said treatment-head unit can be initiated upon such assembly.

17. The unit of claim 1 or claim 1, in combination with a mounting-adapter unit for incorporation in an orthopedic cast, said adapter unit having a central aperture, and said housing and said adapter unit having co-acting locking formations arrayed about said transducer and about said central aperture, whereby upon locking engagement of said treatment-head unit to said adapter unit that has been incorporated into an orthopedic cast, said transducer is held by said treatment-head unit and by said adapter unit in local body-confronting relation to a body locale that is otherwise surrounded by the orthopedic cast, said locking formations being of bayonet-locking variety.

18. The unit of claim 7 or claim 1, in combination with a mounting-adapter unit for incorporation in an orthopedic cast, said adapter unit having a central aperture, and said housing and said adapter unit having co-acting locking formations arrayed about said transducer and about said central aperture, whereby upon locking engagement of said treatment-head unit to said adapter unit that has been incorporated into an orthopedic cast, said tranducer is held by said treatment-head unit and by said adapter unit in local body-confronting relation to a body locale that is otherwise surrounded by the orthopedic cast, said locking formations of both said treatment-head unit and said adapter unit being symmetrically arrayed about said transducer.

19. The unit of claim 7 or claim 1, in combination with a remote-control unit wherein flexible fiber-optic means provide the only interconnection of said treatment-head unit to said remote-control unit, said fiber-optic menas including a coupling of said remote-control unit to said photo-sensitive device, said remote-control unit containing (a) a light source adapted to irradiate one end of said fiber-optic coupling and (b) means for modulating light from said source, whereby operation of said transducer is controlled by modulated light from said light source.

20. The unit of claim 7 or claim 1, in combination with a remote-control unit wherein flexibe fiber-optic means provide the only interconnection of said treatment-head unit to said remote-control unit, said fiber-optic means including a coupling of said remote-control unit to said photo-sensitive device, said remote-control unit containing (a) a light source adapted to irradiate one end of said fiber-optic coupling and (b) menas for modulating light from said source, whereby operation of said transducer is controlled by modulated light from said light source, signal monitoring means within said housing for producing an output signal upon generator-output failure to meet a predetermined criterion, a light source in said housing for externally communicating the existence of such failure, said remote-control unit including a monitoring photo-sensitve element, said fiber-optic means including a further coupling of the monitoring photo-sensitive element to the light source in said housing, and an electrical connection from said monitoring photo-sensitive element the light source in said remote-control unit for disabling modulated-light transmission to said treatment-head unit in the event of such failure.

21. The unit of claim 7 or claim 1, in combination with a remote-control unit wherein flexible fiber-optic means provide the only interconnection of said treatment-head unit to said remote-control unit, said fiber-optic means including a coupling of said remote-control unit to said photo-sensitive device, said remote-control unit containing (a) a light source adapted to irradiate one end of said fiber-optic coupling and (b) means for modulating light from said source, whereby operation of said transducer is controlled by modulated light transmitted from said light source, signal monitoring means within said housing for producing an output signal upon generator-output failure to meet a predetermined criterion, 22. The unit of claim 7 or claim 1, in combination with a mounting-adapter unit for incorporation in an orthopedic cast, said adapter unit having a central aperture, and said housing and said adapter unit having coacting locking formations arrayed about said transducer and about said central aperture, whereby upon locking engagement to said adapter unit that has been incorporated into an orthopedic cast, said transducer is held by said adapter unit in local body-confronting relation to a body locale that is otherwise surrounded by the orthopedic cast, at least one normally open unactuated switch being mounted to said housing and including an actuating button which projects away from said housing for inward switch-closing actuation upon assembly to said adapter unit, and said switch when in closed condition having a control connection for enabling electrical excitation of said transducer.

23. For use in the treatment of living tissue and/or cells with ultrasonic radiation, a self-contained treatment-head unit comprising a housing having an external-access port, an ultrasonic generator and a power source connected to said generator and contained within said housing, an ultrasonic transducer connected to said generator and having an active body-application face exposed externally of said housing, said generator being specifically tuned for efficient coupling to said transducer, and control means for said generator including photo-sensitive device means carried within said housing and adapted via said port to produce control signals governing operation of said generator; the active face of said transducer being mounted to a flat protective panel of a material that is transparent to ultrasonic radiation by said transducer, whereby said panel is the effective body-application face of said transducer, said panel being the closed end of a cupped shell having compliantly yieldable telescoping fit to said housing, said cupped shell having a second panel spaced from said protective panel and from said transducer, and a foamed plastic body abutting said second panel and contained within said shell and a portion of said housing to provide compliant yieldability of said telescoping fit.

24. The unit of claim 7 or claim 23, in which said transducer is a thin piezoelectric disc.

25. The unit of claim 7 or claim 23, in which said transducer is a thin piezoelectric disc of lead/zirconium/titanate variety.

26. For use in the treatment of living tissue and/or cells with ultrasonic radiation, a self-contained treatment-head unit comprising a housing having an external-access port, an ultrasonic generator and a power source connected to said generator and contained within said housing, an ultrasonic transducer connected to said generator and having an active body-application face exposed externally of said housing, said generator being specifically tuned for efficient coupling to said transducer, and control means for said generator including photo-sensitive device means carried within said housing and adapted via said port to produce control signal governing operation of said generator; the active face of said transducer being mounted to a flat protective panel of material that is transparent to ultrasonic radiation by said transducer, whereby said panel is the effective body-application face of said transducer, said panel being the closed end of a cupped shell having a compliantly yieldable telescoping fit to said housing, said telescoping fit being relatively loose so as to afford a range of compliantly yieldable body-adapting angular displacement of said panel with respect to said housing.

27. The unit of claim 26, and including a foamed plastic body contained within said shell and within a portion of said housing to provide the compliant yieldability of said telescoping fit.

28. The unit of claim 26, and a flexible protective sleeve peripherally fixed to said shell near the closed nd of said shell and in at least partial overlap with said housing at the region of telescoping fit.

* * * * *